US010774055B2

(12) United States Patent
Pillai et al.

(10) Patent No.: US 10,774,055 B2
(45) Date of Patent: Sep. 15, 2020

(54) PROCESS FOR PREPARING 1,1,3-TRIOXO-1,2-BENZOTHIAZOLE-6-CARBOXAMIDE

(71) Applicants: Bijukumar Gopinathan Pillai, Gujarat (IN); Sima Mirilashvili, Lod (IL); Yaniv Barda, Rehovot (IL); Bhavinkumar P. Hamirani, Gujarat (IN); Bhoopal Meka, Telengana (IN); Sreedevi Mannam, Telengana (IN)

(72) Inventors: Bijukumar Gopinathan Pillai, Gujarat (IN); Sima Mirilashvili, Lod (IL); Yaniv Barda, Rehovot (IL); Bhavinkumar P. Hamirani, Gujarat (IN); Bhoopal Meka, Telengana (IN); Sreedevi Mannam, Telengana (IN)

(73) Assignee: Adam Agan Ltd., Ashdod (IL)

( * ) Notice: Subject to any disclaimer, the term of this patent is extended or adjusted under 35 U.S.C. 154(b) by 239 days.

(21) Appl. No.: 16/066,965

(22) PCT Filed: Dec. 28, 2016

(86) PCT No.: PCT/IB2016/001927
§ 371 (c)(1),
(2) Date: Jun. 28, 2018

(87) PCT Pub. No.: WO2017/115137
PCT Pub. Date: Jul. 6, 2017

(65) Prior Publication Data
US 2020/0157067 A1    May 21, 2020

(30) Foreign Application Priority Data
Jan. 1, 2016  (IN) .............................. 201631000085

(51) Int. Cl.
*C07D 275/06* (2006.01)
*C07D 239/69* (2006.01)

(52) U.S. Cl.
CPC .......... *C07D 275/06* (2013.01); *C07D 239/69* (2013.01)

(58) Field of Classification Search
CPC ..................................................... C07D 275/06
See application file for complete search history.

(56) References Cited

U.S. PATENT DOCUMENTS 4,302,241 A    11/1981  Levitt

FOREIGN PATENT DOCUMENTS

CN    103 333 120 A    10/2013

OTHER PUBLICATIONS

G.B. Jackman et al. "Studies in the Field of Diuretic Agents. Part VI Some Sulphamoylbenzoic Acids", Journal of Pharmacy and Pharmacology, vol. 14, No. 1, Sep. 12, 1962, pp. 679-686.
Xu L. et al. "Oxidative cyclization of N-alkyl-o-methyl-arenesulfonamides to biologically important saccharin derivatives", Tetrahedron, Elsevier Science Publishers, Amsterdam, NL, vol. 62, No. 33, Aug. 14, 2006, pp. 7902-7910.
International Search Report dated Mar. 16, 2017 in connection with PCT/IB2016/001927.
Written Opinion of the International Searching Authority dated Mar. 16, 2017 in connection with PCT/IB2016/001927.

*Primary Examiner* — Laura L Stockton
(74) *Attorney, Agent, or Firm* — Gary J. Gershik; Cooper & Dunham LLP

(57) ABSTRACT

A process for preparing, 1,1,3-trioxo-1,2-benzothiazole-6-carboxamide of formula (I) comprising: (a) oxidizing 2,5-dimethyl-benzenesulfonamide of formula (II) in the presence of an oxidizing agent to receive 2-sulfamoyl-terephthalic acid of formula (III); (b) converting the formed 2-sulfamoyl-terephthalic acid of formula (III) to receive 2-sulfamoyl-terephthalic acid derivative of formula (IV); and (c) reacting the resulting 2-sulfamoyl-terephthalic acid derivative of formula (IV) with ammonia ($NH_3$) or ammonium containing-salt; wherein R represents OR' or Cl and R' represents a branched or non-branched $C_1$-$C_{12}$ alkyl.

14 Claims, No Drawings

PROCESS FOR PREPARING 1,1,3-TRIOXO-1,2-BENZOTHIAZOLE-6-CARBOXAMIDE

CROSS-REFERENCE TO RELATED APPLICATIONS

This application is a § 371 national stage of PCT International Application No. PCT/IB2016/001927, filed Dec. 28, 2016 and claims priority of Indian Provisional Application No. 201631000085, filed Jan. 1, 2016, the entire contents of each of which are hereby incorporated by reference.

TECHNICAL FIELD

The present subject matter relates to a process for preparing 1,1,3-trioxo-1,2-benzothiazole-6-carboxamide.

BACKGROUND

The compound 1,1,3-trioxo-1,2-benzothiazole-6-carboxamide of formula (I) is an important intermediate for preparing inter cilia the herbicidal agents such as mesosulfuron-methyl.

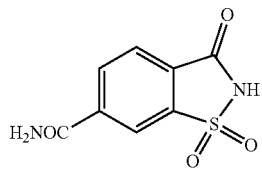

(I)

CN 103333120 describes a process for preparing mesosulfuron-methyl from p-toluic acid via the intermediate 1,2-benzisothiazole-6-carboxamide,2,3-dihydro-3-oxo-,1,1-dioxide. Chromates which are hazardous reagents are used in the oxidation step.

CN 104610167 describes a process for preparing mesosulfuron-methyl which includes the steps of reduction of 6-nitrosaccharin to obtain 6-amino saccharin under a condition that reduction catalyst exists and diazotization of the 6-amino saccharin to obtain 6-isonitrosomethyl.

CN 103755603 describes the preparation of methyl-2-sulfamoyl-4-(methylsulfonamidomethyl)benzoate by the following steps: a reaction of p-(methylsulfonamidomethyl)toluene and chlorosulfonation agent (chlorosulfonic acid) at (−10)-0° C., and performing ammonolysis reaction in ammonia water at room temperature, to obtain 2-sulfamoyl-4-(methylsulfonamidomethyl)toluene; (2) oxidizing with potassium dichromate in concentrated sulfuric acid at (−4)-(−2)° C., to obtain 5-(methylsulfonamidomethyl)saccharin; and (3) dissolving in methanol, adding concentrated sulfuric acid, and performing alcoholysis reaction.

Based on the disadvantages in the above processes, it would be highly desirable to have an improved process for the production of the compound of formula (I) which is suitable for industrial use, highly efficient, low-cost, environmentally friendly, and provides a high yield in a relatively short reaction time, thereby overcoming the deficiencies of the prior art. The present subject matter provides such a process.

It is therefore a purpose of the present subject matter to provide a process that overcomes the disadvantages of the known art.

SUMMARY

According to one aspect, the present subject matter provides a process for preparing 1,1,3-trioxo-1,2-benzothiazole-6-carboxamide of formula (I) or a salt thereof

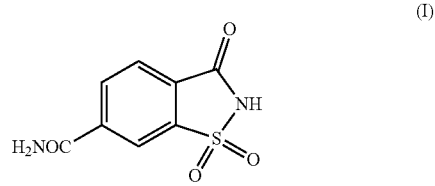 [SMILES: NC(=O)c1ccc2c(c1)S(=O)(=O)NC2=O]

(I)

by oxidizing 2,5-dimethyl-benzenesulfonamide of formula (II) or a salt thereof;

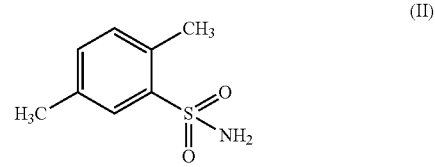

(II)

in the presence of an oxidizing agent to obtain 2-sulfamoyl-terephthalic acid of formula (III) or a salt thereof;

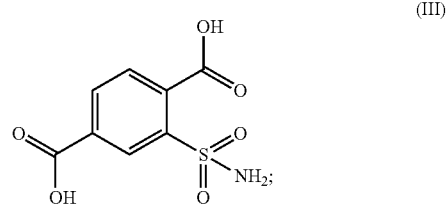 [SMILES: NS(=O)(=O)c1cc(C(=O)O)ccc1C(=O)O]

(III)

(b) converting the formed 2-sulfamoyl-terephthalic acid of formula (III) to obtain 2-sulfamoyl-terephthalic acid derivative of formula (IV) or a salt thereof;

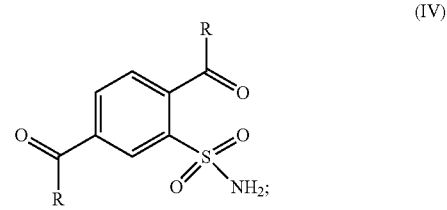

(IV)

(c) reacting the resulting 2-sulfamoyl-terephthalic acid derivative of formula (IV) with ammonia ($NH_3$) or ammonium containing-salt, wherein R represents OR' or Cl; and R' represents a branched or non-branched $C_1$-$C_{12}$ alkyl.

According to an embodiment, the oxidizing agent may be selected from the group consisting of oxygen, air, ozone, hydrogen peroxide, inorganic peroxides, nitric acid, nitrate compounds, sulfuric acid, peroxydisulfuric acid, peroxymonosulfuric acid, chlorite compounds, chlorate compounds, perchlorate compounds, sodium hypochlorite, calcium hypochlorite, potassium permanganate, chromate compounds and dichromate compounds. According to an embodiment, the oxidation may be carried out in the presence of a catalyst. The catalyst may be selected from the group consisting of bis(Bipyridine)Nickel(II) dichloride and bis(Bipyridine)Nickel(II) hydrochloride.

According to another embodiment, at least one of the compound of formula (I), the compound of formula (II), the compound of formula (III) and the compound of formula (IV) are in the form of a salt selected from the group consisting of ammonia salt, sodium salt, potassium salt, calcium salt and magnesium salt. The conversion may be carried out in the presence of (i) one of thionyl chloride, oxalyl chloride, phosgene, triphosgene, and (ii) an alcohol with the formula R'OH, wherein R' represents a branched or non-branched $C_1$-$C_{12}$ alkyl. In another embodiment, the conversion is carried out in the presence of an acid selected from the group consisting of sulfuric acid, hydrochloric acid, nitric acid, hydroiodic acid and p-toluene sulfonic acid, and an alcohol with the formula R'OH, wherein R' represents a branched or non-branched $C_1$-$C_{12}$ alkyl. In a further embodiment, the conversion may be carried out in the presence of one of thionyl chloride, oxalyl chloride, phosgene and triphosgene.

The ammonium containing-salt may be selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide and ammonia ($NH_3$).

According to another embodiment, the molar ratio of the compound of formula (IV) to the ammonia or ammonium-containing salt may be from 1:2 to 1:50. The resulting compound of formula (I) may be present at a purity of at least 70%, at least 75%, at least 80%, at least 85%, at least 90%, at least 95%, at least 98%, or at least 99%.

According to a further embodiment, the compound of formula (II) may be prepared by the chlorination of 2,5-dimethyl-benzenesulfonic acid of formula (V)

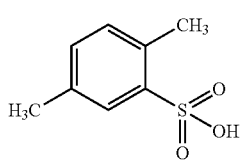

(V)

and subsequent amination of the resulting 2,5-dimethyl-benzenesulfonyl chloride of formula (VI)

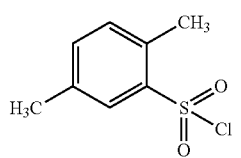

(VI)

The chlorination may be carried out in the presence of a chlorination agent selected from the group consisting of phosphorus oxychloride, thionyl chloride, phosgene, sulfuryl chloride, phosphorus pentachloride, triphosgene, diphosgene and oxalyl chloride. The amination may be carried out in the presence of an amination agent selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide and ammonia ($NH_3$).

According to a further aspect, the present subject matter provides a process for preparing 1,1,3-trioxo-1,2-benzothiazole-6-carboxamide of formula (I) or a salt thereof

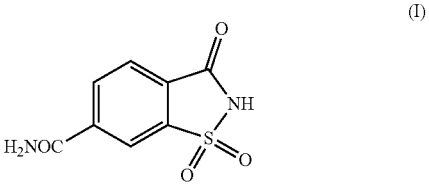 [SMILES: NC(=O)c1ccc2c(c1)S(=O)(=O)NC2=O]

(I)

by chlorinating 2,5-dimethyl-benzenesulfonic acid of formula (V)

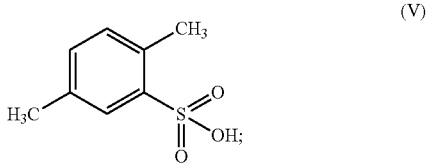

(V)

(b) aminating the resulting 2,5-dimethyl-benzenesulfonyl chloride of formula (VI)

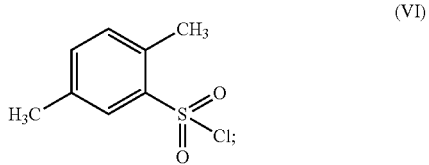

(VI)

(c) oxidizing the resulting 2,5-dimethyl-benzenesulfonamide of formula (II) or a salt thereof;

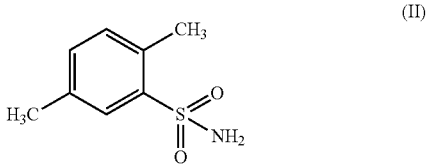

(II)

in the presence of an oxidizing agent and to obtain 2-sulfamoyl-terephthalic acid of formula (III) or a salt thereof;

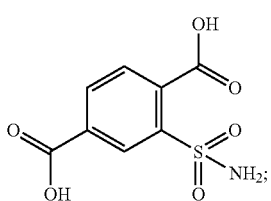

(d) converting the formed 2-sulfamoyl-terephthalic acid of formula (III) to obtain 2-sulfamoyl-terephthalic acid derivative of formula (IV) or a salt thereof;

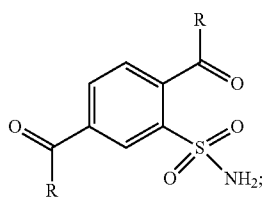

and (e) reacting the resulting 2-sulfamoyl-terephthalic acid derivative of formula (IV) with ammonia ($NH_3$) or ammonium containing-salt, wherein R represents OR' or Cl; and R' represents a branched or non-branched $C_1$-$C_{12}$ alkyl.

According to an embodiment, the oxidizing agent may be selected from the group consisting of oxygen, air, ozone, hydrogen peroxide, inorganic peroxides, nitric acid, nitrate compounds, sulfuric acid, peroxydisulfuric acid, peroxymonosulfuric acid, chlorite compounds, chlorate compounds, perchlorate compounds, sodium hypochlorite, calcium hypochlorite, potassium permanganate, chromate compounds and dichromate compounds.

According to an embodiment, the oxidation may be carried out in the presence of a catalyst. The catalyst may be selected from the group consisting of bis(Bipyridine)Nickel (II) dichloride and bis(Bipyridine)Nickel(II) hydrochloride.

According to another embodiment, at least one of the compound of formula (I), the compound of formula (II), the compound of formula (III) and the compound of formula (IV) are in the form of a salt selected from the group consisting of ammonia salt, sodium salt, potassium salt, calcium salt and magnesium salt. The conversion may be carried out in the presence of (i) one of thionyl chloride, oxalyl chloride, phosgene, triphosgene, and (ii) an alcohol with the formula R'OH, wherein R' represents a branched or non-branched $C_1$-$C_{12}$ alkyl. In another embodiment, the conversion is carried out in the presence of an acid selected from the group consisting of sulfuric acid, hydrochloric acid, nitric acid, hydroiodic acid and p-toluene sulfonic acid, and an alcohol with the formula R'OH, wherein R' represents a branched or non-branched $C_1$-$C_{12}$ alkyl. In a further embodiment, the conversion may be carried out in the presence of one of thionyl chloride, oxalyl chloride, phosgene and triphosgene.

The ammonium containing-salt may be selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide and ammonia ($NH_3$).

According to another embodiment, the molar ratio of the compound of formula (IV) to the ammonia or ammonium-containing salt may be from 1:2 to 1:50. The resulting compound of formula (I) may be present at a purity of at least 70%, at least 75%, at least 80%, at least 85%, at least 90%, at least 95%, at least 98%, or at least 99%.

According to a further embodiment, the chlorination may be carried out in the presence of a chlorination agent selected from the group consisting of phosphorus oxychloride, thionyl chloride, phosgene, sulfuryl chloride, phosphorus pentachloride, triphosgene, diphosgene and oxalyl chloride. The amination may be carried out in the presence of an amination agent selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide, and ammonia ($NH_3$).

In an embodiment, the herein described processes may be used in the production of mesosulfuron-methyl.

In another embodiment, the present subject matter relates to the use of the compound of formula (I) as prepared according to processes disclosed herein in the preparation of mesosulfuron-methyl.

DETAILED DESCRIPTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, used of the term "about" herein specifically includes ±10% from the indicated values in the range. In addition, the endpoints of all ranges directed to the same component or property herein are inclusive of the endpoints, are independently combinable, and include all intermediate points and ranges.

Process for Preparing 1,1,3-trioxo-1,2-benzothiazole-6-carboxamide

The present subject matter provides a process for preparing 1,1,3-trioxo-1,2-benzothiazole-6-carboxamide of formula (I) or a salt thereof

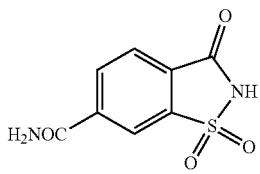
(I)

wherein the process comprises
(a) oxidizing 2,5-dimethyl-benzenesulfonamide of formula (II) or a salt thereof;

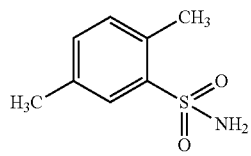
(II)

in the presence of an oxidizing agent and to receive 2-sulfamoyl-terephthalic acid of formula (III) or a salt thereof;

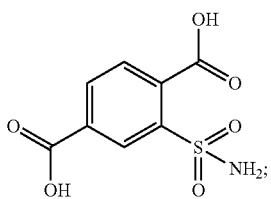
(III)

(b) converting the formed 2-sulfamoyl-terephthalic acid of formula (III) to receive 2-sulfamoyl-terephthalic acid derivative of formula (IV) or a salt thereof;

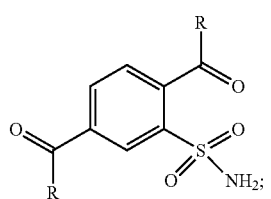
(IV)

and
(c) reacting the resulting 2-sulfamoyl-terephthalic acid derivative of formula (IV) with ammonia (NH$_3$) or ammonium containing-salt, wherein R represents OR' or Cl; and R' represents a branched or non-branched C1-C12 alkyl. In a preferred embodiment, R' may be defined as methyl or ethyl.

In another embodiment, the present subject matter provides a process for preparing 1,1,3-trioxo-1,2-benzothiazole-6-carboxamide of formula (I) or a salt thereof

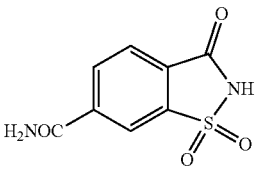
(I)

wherein the process comprises
(a) chlorinating 2,5-dimethyl-benzenesulfonic acid of formula (V);

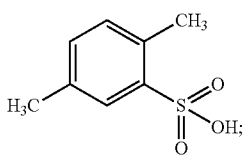
(V)

(b) aminating the resulting 2,5-dimethyl-benzenesulfonyl chloride of formula (VI);

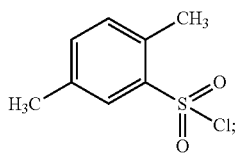
(VI)

(c) oxidizing 2,5-dimethyl-benzenesulfonamide of formula (II) or a salt thereof;

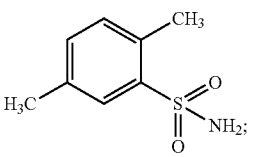
(II)

in the presence of an oxidizing agent to receive 2-sulfamoyl-terephthalic acid of formula (III) or a salt thereof;

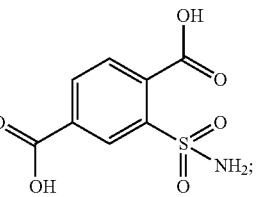
(III)

(d) converting the formed 2-sulfamoyl-terephthalic acid of formula (III) to receive 2-sulfamoyl-terephthalic acid derivative of formula (IV) or a salt thereof;

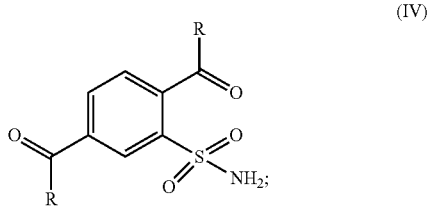

and (e) reacting the resulting 2-sulfamoyl-terephthalic acid derivative of formula (IV) with ammonia (NH$_3$) or ammonium containing-salt, wherein R represents OR' or Cl; and R' represents a branched or non-branched C$_1$-C$_{12}$ alkyl. In a preferred embodiment, R' may be defined as methyl or ethyl.

The resulting compound of formula (IV) is subsequently reacted with ammonia (NH$_3$) or ammonium containing-salt to form the compound of formula (I). According to an embodiment, the compound of formula (IV) is isolated prior to its reaction with the ammonia or ammonium-containing salt. According to another embodiment, the compound of formula (IV) is not isolated prior to its reaction with the ammonia or ammonium-containing salt.

In an embodiment of the present process, the oxidizing agent is selected from the group consisting of but not limited to oxygen, air, ozone, hydrogen peroxide, inorganic peroxides, nitric acid, nitrate compounds, sulfuric acid, peroxydisulfuric acid, peroxymonosulfuric acid, chlorite compounds, chlorate compounds, perchlorate compounds, sodium hypochlorite, calcium hypochlorite, potassium permanganate, chromate compounds and dichromate compounds. In a specific example, the oxidizing agent is sodium hypochlorite.

In one embodiment, the oxidation of 2,5-dimethyl-benzenesulfonamide of formula (II) in order to obtain 2-sulfamoyl-terephthalic acid of formula (III) is performed in the presence of a catalyst selected from the group consisting of but not limited to bis(Bipyridine)Nickel(II) dichloride and bis(Bipyridine)Nickel(II) hydrochloride. In a specific embodiment, the catalyst may be (Bipyridine)Nickel(II) Hydrochloride.

The present process is advantageous in that it avoids the need for using hazardous reagents such as chromates. The present process furthermore provides a shorter reaction time. In addition, the process is highly efficient providing higher yields and purities of 1,1,3-trioxo-1,2-benzothiazole-6-carboxamide thus leading to higher yields and purities of the final product, as compared to the methods known in the prior art.

According to an embodiment, the oxidation of 2,5-dimethyl-benzenesulfonamide of formula (II) in order to obtain 2-sulfamoyl-terephthalic acid of formula (III) also produces 1,1,3-trioxo-1,2-benzothiazole-6-carboxylic acid of formula (VII).

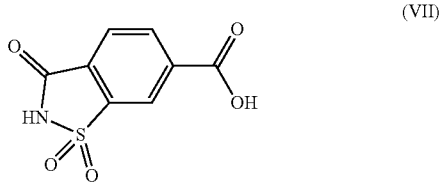

In some embodiments, 1,1,3-trioxo-1,2-benzothiazole-6-carboxylic acid may be produced in amounts of as much as 50%. Although 1,1,3-trioxo-1,2-benzothiazole-6-carboxylic acid is not the desired product of the oxidation reaction, it may be beneficial to use this compound in further steps in the production of mesosulfuron-methyl. According to an embodiment, 1,1,3-trioxo-1,2-benzothiazole-6-carboxylic acid may undergo the conversion step as described hereinabove to produce the compound of formula (IV). According to another embodiment, 1,1,3-trioxo-1,2-benzothiazole-6-carboxylic acid may be reacted with phosphorus pentachloride in toluene and subsequently reacted with ammonia or an ammonium-containing salt to form the compound of formula (I).

In an embodiment of the present processes, the molar ratio between the compound of formula (IV) and the ammonia or ammonium-containing salt is from about 1:2 to about 1:100. In another embodiment, the molar ratio between the compound of formula (IV) and the ammonia or ammonium-containing salt is from about 1:2 to about 1:50. In yet another embodiment, the molar ratio between the compound of formula (IV) and the ammonia or ammonium-containing salt is from about 1:2 to about 1:30. In a further embodiment, the molar ratio between the compound of formula (IV) and the ammonia or ammonium-containing salt is from about 1:2 to about 1:20. In a specific embodiment, the molar ratio between the compound of formula (IV) and the ammonia or ammonium-containing salt is about 1:10.

In an embodiment of the present processes, the molar ratio between the catalyst and the compound of formula (II) is from about 1:2 to about 1:100. In another embodiment, the molar ratio between the catalyst and the compound of formula (II) is from about 1:2 to about 1:50. In yet another embodiment, the molar ratio between the catalyst and the compound of formula (II) is from about 1:2 to about 1:25. In a further embodiment, the molar ratio between the catalyst and the compound of formula (II) is from about 1:2 to about 1:15. In a specific embodiment, the molar ratio between the catalyst and the compound of formula (II) about 1:10.

In an embodiment of the present process, the compound of formula (I), the compound of formula (II), the compound of formula (III) and the compound of formula (IV) are in the form of a salt. Examples of salts may include but are not limited to ammonia salt, sodium salt, potassium salt, calcium salt and magnesium salt.

According to an embodiment, the conversion step is an esterification step and is carried out in the presence of (i) one of thionyl chloride, oxalyl chloride, phosgene, triphosgene, and (ii) an alcohol with the formula R'OH, wherein R' represents a branched or non-branched C$_1$-C$_{12}$ alkyl. In another embodiment, the esterification is carried out in the presence of an acid selected from the group consisting of sulfuric acid, hydrochloric acid, nitric acid, hydroiodic acid and p-toluene sulfonic acid, and an alcohol with the formula R'OH, wherein R' represents a branched or non-branched C$_1$-C$_{12}$ alkyl. In a preferred embodiment, the esterification is performed in methanol or ethanol in the presence of sulfuric acid.

According to another embodiment, the conversion is carried out in the presence of one of thionyl chloride, oxalyl chloride, phosgene and triphosgene.

In an embodiment of the present process, the ammonium containing-salt is selected from the group consisting of but not limited to ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide and ammonia gas. In a specific example, 2-sulfamoyl-terephthalic acid derivative of formula (IV) is reacted with ammonium hydroxide to form 1,1,3-trioxo-1,2-benzothiazole-6-carboxamide of formula (I).

In one embodiment, the reaction to form the compound of formula (I) from the compound of formula (IV) is initially conducted at a temperature from about 20° C. to about 100° C., preferably from about 25° C. to about 80° C., more preferably from about 50° C. to about 70° C., and subsequently cooled to a temperature of about 1° C. to about 25° C., preferably from about 3° C. to about 20° C., more preferably from about 5° C. to about 10° C. In a preferred embodiment, the reaction is conducted at an initial temperature from about 55° C. to about 60° C. and subsequently cooled to a temperature of about 5° C. to about 10° C.

In one embodiment, the oxidation reaction to form the compound of formula (III) from the compound of formula (II) is conducted at a temperature from about 20° C. to about 100° C., preferably from about 30° C. to about 70° C., more preferably from about 30° C. to about 50° C. In a preferred embodiment, the reaction is conducted at a temperature from about 35° C. to about 40° C.

According to an embodiment, the resultant compound of formula (I) is present at a purity of at least 80%, at least 85%, at least 88%, at least 89%, at least 90%, at least 91%, at least 92%, at least 93%, at least 94%, at least 95%, at least 96%, at least 97%, at least 98%, or at least 99%.

In another embodiment the present subject matter provides a process for preparing 2,5-dimethyl-benzenesulfonamide of formula (II) wherein the process comprises the chlorination of 2,5-dimethyl-benzenesulfonic acid of formula (V)

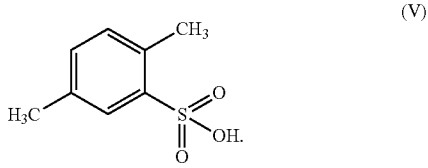

(V)

and subsequent amination of the resulting 2,5-dimethyl-benzenesulfonyl chloride of formula (VI);

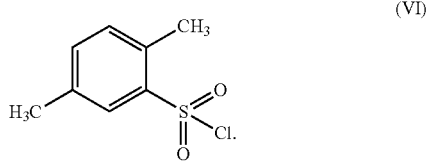

(VI)

2,5-dimethyl-benzenesulfonic acid of formula (V) may be synthesized by known methods. JP 2003-382264 and JP 2010-247881 describe the process of obtaining 2,5-dimethyl-benzenesulfonic acid from p-xylene.

According to an embodiment, the chlorination step is carried out in the presence of a chlorination agent selected from the group consisting of but not limited to phosphorus oxychloride, thionyl chloride, phosgene, sulfuryl chloride, phosphorus pentachloride, triphosgene, diphosgene and oxalyl chloride. In a specific example, the chlorination agent is thionyl chloride.

According to an embodiment, the amination step is carried out in the presence of an amination agent selected from the group consisting of but not limited to ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide, and ammonia ($NH_3$). In a specific example, the amination agent is ammonium hydroxide.

The compound of formula (I) is an important intermediate and is used in the preparation of mesosulfuron-methyl, as described in CN 103333120 incorporated herein by reference in its entirety.

In a further aspect of the subject matter there is provided a process for preparation of mesosulfuron-methyl comprising:
a) preparing compound of formula (I) as described herein;
b) providing reaction conditions for preparation of mesosulfuron-methyl.

According to an embodiment the reaction conditions in step (b) include but are not limited to oxidation, reduction, ring opening, sulfonylation and coupling to obtain mesosulfuron-methyl.

The progress of the reaction can be monitored using any suitable method, which can include, for example, chromatographic methods such as, e.g., high performance liquid chromatography (HPLC), thin layer chromatography (TLC), and the like.

In yet another embodiment, the compound of formula (I) can be isolated from the reaction mixture by any conventional techniques well-known in the art. Such isolation techniques can be selected, without limitation, from the group consisting of concentration, extraction, precipitation, cooling, filtration, crystallization, centrifugation, and a combination thereof, followed by drying.

In yet another embodiment, the compound of formula (I) can be optionally purified by any conventional techniques well-known in the art. Such purification techniques can be selected, without limitation, from the group consisting of precipitation, crystallization, extraction, slurrying, washing in a suitable solvent, filtration through a packed-bed column, dissolution in an appropriate solvent, re-precipitation by addition of a second solvent in which the compound is insoluble, and a combination thereof.

The following examples illustrate the practice of the present subject matter in some of its embodiments, but should not be construed as limiting the scope of the present subject matter. Other embodiments will be apparent to one skilled in the art from consideration of the specification and examples. It is intended that the specification, including the examples, is considered exemplary only without limiting the scope and spirit of the present subject matter.

Example 1

An exemplary experimental procedure for producing,1,3-trioxo-1,2-benzothiazole-6-carboxamide of formula (I) is described as follows:

Step 1: Preparation of
2,5-dimethyl-benzenesulfonamide (Compound (II))

200 g (0.9 moles) of 2,5-Dimethyl-benzenesulfonic acid (Compound V) and 428.7 g (3.603 moles) of thionyl chloride were charged in a round bottom flask and stirred for 10 minutes at room temperature. The reaction mixture was heated to 75° C. and stirred for 5 hours until no traces of the starting compound were found. The reaction mixture comprising 2,5-dimethyl-benzenesulfonyl chloride (Compound VI) was cooled to 45° C. and excess thionyl chloride was distilled out under vacuum to obtain a brown oil. The oil was added dropwise to a 472 ml (5.55 moles) solution of 28% ammonia (ammonium hydroxide) and stirred for 6 hours at room temperature. The solid 2,5-dimethyl-benzenesulfonamide (Compound II) was filtered and washed with 1000 ml water. The cake was dried at 60° C.

Yield of 2,5-dimethyl-benzenesulfonamide: 152 g (92%).

Step 2: Preparation of 2-sulfamoyl-terephthalic acid (Compound (III))

40 ml (10.8 mmol) of Ni(BiPy)Cl$_2$ solution and 127 ml (21.6 mmol) of sodium hypochlorite were charged in a round bottom flask. The mixture was stirred at 25-30° C. for 30 minutes until black precipitates were formed. 20 gr (108 mmol) of 2,5-Dimethyl-benzenesulfonamide (Compound II) was added at 25-30° C. and the reaction mixture was stirred for 15 min. 507 ml (1.08 moles) of 127 gr/L Sodium hypochlorite solution was added dropwise at 35-40° C. and the reaction was stirred for 4 hours. The reaction progress was monitored by HPLC until 2,5-dimethyl-benzenesulfonamide (Compound II) was present at a concentration of less than 1%. 80 ml of 38% HCl was added dropwise until pH is highly acidic (pH=1-2) and gas evolution was observed. After which, 80 gr (420.8 mmol) of sodium metabisulfite was added in portions at 20-50° C. until no colorization on starch iodide paper was observed. The reaction mass was cooled to 25-30° C. and stirred for 1 hour at 25° C. The solid formed was filtered, washed with 20 ml water at room temperature and dried in vacuum at 55-60° C.

Yield: 19.99 gr (75.53%). Two major products, were observed namely 2-sulfamoyal terephthalic acid (formula III) (73.63%) and 1,1,3-trioxo-1,2-benzothiazole-6-carboxylic acid (formula VII) (24.76%).

Step 3: Preparation of 2-sulfamoyl-terephthalic acid dimethyl ester (Compound (IV) R=OCH3)

125 gr (510.2 mmol) of 2-Sulfamoyl-terephthalic acid (Compound III) was added to 375 ml methanol at room temperature. 50 gr (510.2 mmol) of sulfuric acid was added slowly and the reaction mixture was heated under reflux to 65° C. for 18-24 hours. The reaction mixture was cooled to 5-10° C. and stirred for 30 minutes. The solid formed was filtered and washed with 60 ml of chilled methanol and dried in vacuum at 50-55° C.

Yield of 2-sulfamoyl-terephthalic acid dimethyl ester: 117.79 gr (82.4%).

Step 4: Preparation of 1,1,3-trioxo-1,2-benzothiazole-6-carboxamide (Compound (I))

110 gr of (402.8 mmol) 2-sulfamoyl-terephthalic acid dimethyl ester (Compound IV) was added to 550 ml (3.146 moles) of 20% ammonium hydroxide and the mixture was heated to 55-60° C. for 4-6 hours. The reaction mixture was cooled to 5-10° C. and stirred at this temperature for 30 minutes. The solid was filtered, washed with 55 ml of chilled 20% ammonium hydroxide and dried at 45-50° C.

Purity of 1,1,3-trioxo-1,2-benzothiazole-6-carboxamide: >97%.

Yield of 1,1,3-trioxo-1,2-benzothiazole-6-carboxamide: 84.9 gr (82.5%).

As demonstrated in the above example, a high yield of 1,1,3-trioxo-1,2-benzothiazole-6-carboxamide may be produced using the process described hereinabove. The results demonstrate a high level efficiency of the reaction.

While the present subject matter has been shown and described with reference to preferred embodiments thereof, it will be understood by those skilled in the art that many alternatives, modifications and variations may be made thereto without departing from the spirit and scope thereof. Accordingly, it is intended to embrace all such alternatives, modifications, and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A process for preparing 1,1,3-trioxo-1,2-benzothiazole-6-carboxamide of formula (I) or a salt thereof

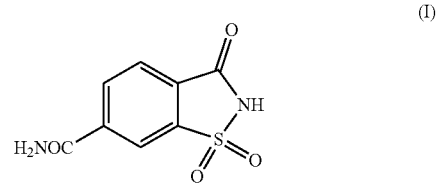 [SMILES: NC(=O)c1ccc2c(c1)S(=O)(=O)NC2=O]

the process comprising:
(a) oxidizing 2,5-dimethyl-benzenesulfonamide of formula (II) or a salt thereof;

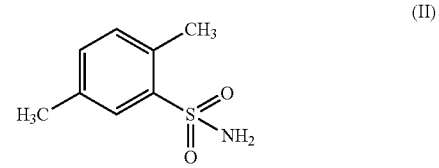

in the presence of an oxidizing agent to obtain 2-sulfamoyl-terephthalic acid of formula (III) or a salt thereof;

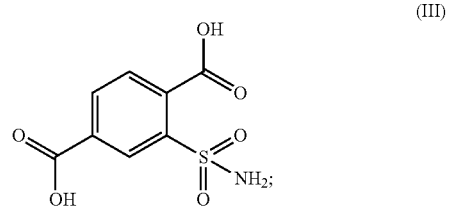 [SMILES: NS(=O)(=O)c1cc(C(=O)O)ccc1C(=O)O]

(b) converting the formed 2-sulfamoyl-terephthalic acid of formula (III) to obtain 2-sulfamoyl-terephthalic acid derivative of formula (IV) or a salt thereof;

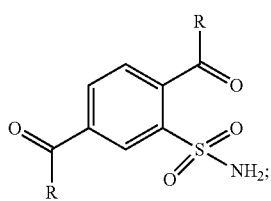

and (c) reacting the resulting 2-sulfamoyl-terephthalic acid derivative of formula (IV) with ammonia (NH₃) or ammonium containing-salt;

wherein R represents OR' or Cl and R' represents a branched or non-branched $C_1$-$C_{12}$ alkyl.

2. The process of claim 1, wherein the oxidizing agent is selected from the group consisting of oxygen, air, ozone, hydrogen peroxide, inorganic peroxides, nitric acid, nitrate compounds, sulfuric acid, peroxydisulfuric acid, peroxymonosulfuric acid, chlorite compounds, chlorate compounds, perchlorate compounds, sodium hypochlorite, calcium hypochlorite, potassium permanganate, chromate compounds and dichromate compounds.

3. The process of claim 1, wherein the oxidizing in carried out in the presence of a catalyst.

4. The process of claim 3, wherein the catalyst is selected from the group consisting of bis(Bipyridine)Nickel(II) dichloride and bis(Bipyridine)Nickel(II) hydrochloride.

5. The process of claim 1, wherein at least one of the compound of formula (I), the compound of formula (II), the compound of formula (III) and the compound of formula (IV) are in the form of a salt wherein the salt is selected from the group consisting of ammonia salt, sodium salt, potassium salt, calcium salt and magnesium salt.

6. The process of claim 1, wherein the conversion is carried out in the presence of (i) one of thionyl chloride, oxalyl chloride, phosgene or triphosgene and (ii) an alcohol with the formula R'OH, wherein R' represents a branched or non-branched $C_1$-$C_{12}$ alkyl.

7. The process of claim 1, wherein the conversion is carried out in the presence of an acid selected from the group consisting of sulfuric acid, hydrochloric acid, nitric acid, hydroiodic acid and p-toluene sulfonic acid, and an alcohol with the formula R'OH, wherein R' represents a branched or non-branched $C_1$-$C_{12}$ alkyl.

8. The process of claim 1, wherein the conversion is carried out in the presence of one of thionyl chloride, oxalyl chloride, phosgene or triphosgene.

9. The process of claim 1, wherein the ammonium con-taining-salt is selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide and ammonia (NH₃).

10. The process of claim 1, wherein the molar ratio of the compound of formula (IV) to the ammonia or ammonium-containing salt is from 1:2 to 1:50.

11. The process of claim 1, wherein the resulting compound of formula (I) is present at a purity of at least 70%, at least 75%, at least 80%, at least 85%, at least 90%, at least 95%, at least 98%, or at least 99%.

12. The process of claim 1, wherein the compound of formula (II) is prepared by the chlorination of 2,5-dimethylbenzenesulfonic acid of formula (V)

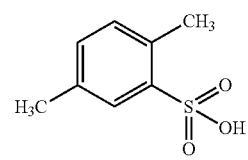

and subsequent amination of the resulting 2,5-dimethylbenzenesulfonyl chloride of formula (VI)

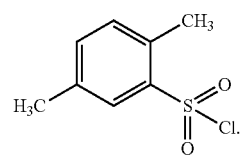

13. The process of claim 12, wherein the chlorination is carried out in the presence of a chlorination agent selected from the group consisting of phosphorus oxychloride, thionyl chloride, phosgene, sulfuryl chloride, phosphorus pentachloride, triphosgene, diphosgene and oxalyl chloride.

14. The process of claim 12, wherein the amination is carried out in the presence of an amination agent selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates, ammonium sulfide and ammonia (NH₃).

* * * * *